US011865536B2

(12) United States Patent
Goyal et al.

(10) Patent No.: US 11,865,536 B2
(45) Date of Patent: Jan. 9, 2024

(54) HUMAN LYMPHOID TISSUE-ON-CHIP

(71) Applicant: President and Fellows of Harvard College, Cambridge, MA (US)

(72) Inventors: Girija Goyal, Cambridge, MA (US); Donald E. Ingber, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 17/730,615

(22) Filed: Apr. 27, 2022

(65) Prior Publication Data
US 2022/0250055 A1 Aug. 11, 2022

Related U.S. Application Data

(63) Continuation of application No. 16/318,591, filed as application No. PCT/US2017/042657 on Jul. 18, 2017, now Pat. No. 11,406,975.

(60) Provisional application No. 62/398,646, filed on Sep. 23, 2016, provisional application No. 62/363,579, filed on Jul. 18, 2016.

(51) Int. Cl.
| | |
|---|---|
| B01L 3/00 | (2006.01) |
| C12N 5/0781 | (2010.01) |
| C12N 5/0783 | (2010.01) |
| A61K 35/28 | (2015.01) |
| A61P 35/00 | (2006.01) |
| A61K 35/17 | (2015.01) |
| C12M 3/06 | (2006.01) |
| A61P 37/04 | (2006.01) |
| C12M 3/00 | (2006.01) |
| A61P 7/00 | (2006.01) |
| C12N 5/00 | (2006.01) |
| C12N 5/0786 | (2010.01) |
| C12N 5/078 | (2010.01) |
| C12N 5/071 | (2010.01) |
| C12N 5/09 | (2010.01) |
| G01N 33/50 | (2006.01) |

(52) U.S. Cl.
CPC .......... *B01L 3/5027* (2013.01); *A61K 35/17* (2013.01); *A61K 35/28* (2013.01); *A61P 7/00* (2018.01); *A61P 35/00* (2018.01); *A61P 37/04* (2018.01); *C12M 21/08* (2013.01); *C12M 23/16* (2013.01); *C12N 5/0018* (2013.01); *C12N 5/069* (2013.01); *C12N 5/0635* (2013.01); *C12N 5/0636* (2013.01); *C12N 5/0645* (2013.01); *C12N 5/0651* (2013.01); *C12N 5/0693* (2013.01); *G01N 33/5011* (2013.01); *B01L 2300/0861* (2013.01); *C12N 2531/00* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 7,807,415 B2 | 10/2010 | Groen | |
| 8,647,861 B2 | 2/2014 | Ingber | |
| 2005/0079556 A1 | 4/2005 | Nixon | |
| 2005/0282148 A1 | 12/2005 | Warren | |
| 2006/0194320 A1 | 8/2006 | Bushnaq-Josting | |
| 2007/0155009 A1 | 7/2007 | McClelland | |
| 2012/0052517 A1 | 3/2012 | Warren | |
| 2012/0149021 A1 | 6/2012 | Yung | |
| 2012/0178097 A1 | 7/2012 | Tai | |
| 2014/0186414 A1* | 7/2014 | Ingber | A61P 7/04 435/2 |
| 2014/0248640 A1 | 9/2014 | Warren | |
| 2014/0342445 A1 | 11/2014 | Ingber | |
| 2015/0203579 A1 | 7/2015 | Papadopoulos | |
| 2015/0260711 A1 | 9/2015 | Toner | |
| 2016/0046896 A1 | 2/2016 | Ingber | |
| 2016/0091489 A1 | 3/2016 | Fan | |

FOREIGN PATENT DOCUMENTS

| | | |
|---|---|---|
| WO | WO 2005/104755 A2 | 11/2005 |
| WO | WO 2008/073635 A2 | 6/2008 |

OTHER PUBLICATIONS

Giese "Human immunity in vitro—Solving immunogenicity and more" (2014) Adv Drug Delivery Rev, 69-70: 103-122. (Year: 2014).*
International Search Report in International Patent Application No. PCT/US2017/042657, dated Nov. 16, 2017 (5 pages).
Written Opinion in International Patent Application No. PCT/US2017/042657, dated Nov. 16, 2017 (14 pages).
Extended European Search Report in European Patent Application No. EP 17831715, dated Jan. 21, 2020 (10 pages).
Singapore Search Report and Written Opinion in Singapore Patent Application No. 11201900422T dated Jun. 4, 2020 (11 pages).
Cupedo, T. et al., "Application of tissue engineering to the immune system: development of artificial lymph nodes," Frontiers in Immunology, vol. 3, p. 343, Nov. 16, 2012.
Giese, C. et al., "Immunological substance testing on human lymphatic micro-organoids in vitro," Journal of Biotechnology, 148(1):38-45, Jul. 1, 2010.
Giese, C. et al., "A Human Lymph Node In Vitro—Challenges and Progress," Artificial Organs, 30(10):803-808, Oct. 6, 2006.
Combined Search and Examination Report in Great Britain Patent Application No. GB2205718.6, dated May 9, 2022 (7 pages).
Moraes, C. et al., "Organs-on-a-chip; a focus on compartmentalized microdevices," Ann. Biomed. Eng. 2012, 40(6): 1211-1227.
Huh, D. et al., "From 3D cell culture to organs-on-chips," Trends Cell Biol., 21(12): 745-754, Dec. 2011.

(Continued)

*Primary Examiner* — Teresa E Knight
(74) *Attorney, Agent, or Firm* — NIXON PEABODY LLP

(57) ABSTRACT

An organ-on-a-chip microfluidic device is disclosed that mimics a human lymph node and/or human lymphoid tissue. The device can include cells from human blood and lymphatic tissue, include an extracellular matrix for the development of immune system components, and provide for the perfusion of fluids and solids resembling blood and lymphatic fluid within micrometer sized channels.

10 Claims, 8 Drawing Sheets

(56) References Cited

OTHER PUBLICATIONS

Hauser, A.E. et al., "Cellular choreography in the germinal center: new visions from in vivo imaging," Semin. Immunolopathol., 32(3): 239-255, Sep. 2010.
Sato, M. et al., "Development of an Ex-vivo lymphatic vascular model," 17th International Conference on Miniaturized Systems for Chemistry and Life Sciences 2013, pp. 1093-1095, 2013.
Battaglia, A. et al., "Lymphocyte populations in human lymph nodes. Alterations in CD4+ CD25+ T regulatory cell phenotype and T-cell receptor Vbeta repertoire," Immunilogy, 110(3): 304-312, Nov. 2003.
Katakai, T. et al., "Lymph node fibroblastic reticular cells construct the stromal reticulum via contact with lymphocytes," J. Exp. Med., 200(6): 783-795, Sep. 2004.
Tehranirokh, M. et al., Microfluidic devices for cell cultivation and proliferation, Biomicrofluidics, 7(5): 51502, Oct. 29, 2013.
Abdelgawad, M. et al., "A fast and simple method to fabricate circular microchanels in polydimethylsiloxane (PDMS)," Lab Chip, 11(3): 545-551, Feb. 2011.

\* cited by examiner

HUMAN LYMPHOID TISSUE-ON-CHIP

CROSS-REFERENCE TO RELATED APPLICATIONS

This application is a continuation of U.S. patent application Ser. No. 16/318,591, filed Jan. 17, 2019, now allowed, which is a U.S. National Stage Entry of International Application No. PCT/US2017/042657, filed Jul. 18, 2017, which claims the benefit of, and priority to, U.S. Provisional Application No. 62/363,579, entitled, "MICROENGINEERED HUMAN LYMPH NODE-ON-CHIP TO STUDY INDUCTION OF IMMUNE RESPONSE TO VARIOUS STIMULI, SUCH AS TUMOR ANTIGENS, PATHOGENS AND VACCINES, AND THE RESPONSE TO IMMUNOTHERAPY IN VITRO," filed Jul. 18, 2016, and U.S. Provisional Application No. 62/398,646, entitled, "MICROENGINEERED HUMAN LYMPH NODE-ON-CHIP TO STUDY INDUCTION OF IMMUNE RESPONSE TO VARIOUS STIMULI, SUCH AS TUMOR ANTIGENS, PATHOGENS AND VACCINES, AND THE RESPONSE TO IMMUNOTHERAPY IN VITRO," filed Sep. 23, 2016, the disclosures of which are hereby incorporated by reference herein in their entireties.

GOVERNMENT SUPPORT

This invention was made with government support under grant number W911NF-12-2-0036 awarded by Defense Advanced Research Projects Agency (DARPA). The government has certain rights in the invention.

TECHNICAL FIELD

The invention relates to a micro-engineered chip and, in particular, to a human lymphoid tissue-on-chip for studying the induction of an immune response to various stimuli, such as tumor antigens, pathogens, and vaccines, and the response to immunotherapy, in vitro.

BACKGROUND

A major bottleneck for research on human immunological responses, and development of immunotherapies, is the lack of correspondence between animal and human studies. Efforts to develop immunotherapy either rely on studies of mouse homologs or humanized mice. Humanized mice have immunocompromising mutations that reduce rejection of the implanted human immune tissue, such as bone marrow, thymus, liver, etc. Despite complicated genetic engineering, treatment with cytokines, and surgery, humanized mice continue to have poor survival, impaired immune responses, and complications from graft versus host disease. Interactions with non-immune cells, such as human endothelial cells, are not captured in humanized mice, and the organization of lymphoid structures is disrupted.

A poignant example of the dissonance between animal models and human immunology is the life threatening cytokine release syndrome caused by the CD28 superagonist TGN1412 in six patients despite extensive animal studies and peripheral blood mononuclear cell (PBMC) testing. Similar lack of predictivity has been described for anticancer antibodies, such as rituximab (anti-CD20) and alemtuzumab (anti-CD52), used to treat B lymphocyte malignancies. Mice do not show the immune-related adverse events seen in patients treated with checkpoint blockade, i.e., treatment with monoclonal antibodies that block surface receptors that inhibit T lymphocyte function. Similarly, humanized mice studies on T lymphocytes reengineered to attack tumors (chimeric antigen receptor-CAR T cells, infused as therapy) do not predict the donor dependent cytokine release syndrome seen in patients.

In vitro culture of PBMCs is the basis of commonly used human assays. However, two-dimensional (2D) culture of PBMCs does not have the necessary three-dimensional (3D) organization and cellular phenotype to mimic the response of organized human immune tissue, such as the tissue found in human lymph nodes. Indeed, the lymph node is the major site of the start of an immune response. It also is the action site of many immunotherapies, including anti-CTLA-4 antibodies that are a major form of therapy used for treatment of human cancers. The lymph node is composed of many cell types present in distinct zones and perfused via a complicated architecture of lymphatic and blood vessels.

There previously have been two published 3D models of the human lymph node: Probiogen's HuALN and VaxDesign's MIMIC system. However, in the HuALN, the T and B lymphocytes are disorganized. Further, although the HuALN shows long-term survival and generation of Immunoglobulin M (IgM) in response to an antigen, there is no generation of Immunoglobulin G (IgG), which suggests that the immune response does not mature. In the MIMIC system, T and B lymphocytes cultured on separate microcarriers are mixed to simulate T-lymphocyte-dependent antibody responses. However, there is no 3D reticular network and the immune response is generated by immigrant dendritic cells. Thus, the MIMIC system does not recapture lymph node anatomy and has not been tested for immunooncology.

Further, blood immune cells are significantly different from tissue resident immune cells, such as immune cells in a tumor, a lymph node, and other areas of the body exclusive of blood. Blood and tissue have different types and proportions of cells, mechanical forces, extracellular matrices, and resulting biological interactions. Indeed, one of the reasons for the TGN1412 cytokine storm was that tissue resident immune cells are hypersensitive to the therapy.

Accordingly, a need exists for better in vitro models of the human lymph node and lymphatic system.

SUMMARY

According to aspects of the present invention, an in vitro model of a human lymph node using organ-on-chip microfluidic culture technology is disclosed. Specifically, an organ-on-a-chip microfluidic device is disclosed that mimics at least some functions of the human lymph node and/or human lymphoid tissue. The device can be seeded with cells from human blood and lymphatic tissue (or cells derived from or related to these cells), include an extracellular matrix for the development of immune system components, optionally allow for the application of mechanical forces (e.g., the pressure of lymph moving from the arm into the lymph node), and provide for the perfusion of fluids and solids resembling blood and lymphatic fluid within fluidic channels.

According to aspects of the present disclosure, a microfluidic device is disclosed. The device includes a body defining a first microchannel and a first chamber. The first microchannel has an inlet and an outlet to an exterior of the body. The first chamber is in fluidic communication with the first microchannel. The device further includes a matrix filling at least a portion of the first chamber, and the matrix includes B lymphocytes.

According to any one or more aspects disclosed herein, the B lymphocytes can be arranged in clusters within said matrix. According to any one or more aspects disclosed herein, the matrix can further include T lymphocytes. According to any one or more aspects disclosed herein, the device can further include a second chamber and a second matrix, with the second matrix filling at least a portion of the second chamber. According to any one or more aspects disclosed herein, said second matrix further can include T lymphocytes. According to any one or more aspects disclosed herein, the B lymphocytes can be arranged in clusters within the matrix. According to any one or more aspects disclosed herein, the matrix can be an extracellular matrix, such as a hydrogel. In some aspects, the extracellular matrix can include a fibrillar network of collagen, laminin, and heparin sulfate proteoglycan. In one or more aspects, the extracellular matrix can be MATRIGEL. According to any one or more aspects disclosed herein, the matrix can be formed of a 50:50 mix of MATRIGEL and culture medium. According to any one or more aspects disclosed herein, the culture medium can be RPMI medium. According to any one or more aspects disclosed herein, the device can further include a reticular network within the matrix to facilitate lymphocyte scanning by one or more of the T lymphocytes or B lymphocytes. According to any one or more aspects disclosed herein, the T lymphocytes and the B lymphocytes can be present within the matrix at a ratio of approximately 60:40. According to any one or more aspects disclosed herein, the T lymphocytes and B lymphocytes can be present within the matrix in an amount of approximately 100,000,000 per milliliter. According to any one or more aspects disclosed herein, at least a portion of the first microchannel can be lined with vascular endothelial cells. According to any one or more aspects disclosed herein, the device can further include a membrane separating the first microchannel from the first chamber, in which the membrane permits fluids and solids to pass between the first microchannel and the first chamber. In one or more aspects, the membrane can be porous. In one or more aspects, the pores can be about 0.4 to 10 μm in diameter. In one or more aspects, the pores can be about 0.4 to 1 μm in diameter. According to any one or more aspects disclosed herein, the body can form a constriction at an interface of the first microchannel and the first chamber to reduce an interface area between the first microchannel and the first chamber as compared to a longitudinal cross-section of the first microchannel and the first chamber. According to any one or more aspects disclosed herein, the clusters can mimic germinal centers within human lymph nodes. According to any one or more aspects disclosed herein, the device can further include one or more microdomains within the matrix formed of microbeads, nanoparticles, or a combination thereof. In one or more aspects, the microdomains can be configured to provide a controlled release of one or more bioactive components to promote three-dimensional organization of the T lymphocytes and the B lymphocytes. According to any one or more aspects disclosed herein, the volume of the matrix can be about 10 μL. According to any one or more aspects disclosed herein, the first microchannel and the first chamber can be about 200 mm long and about 1 mm wide. According to any one or more aspects disclosed herein, the body can define further a second microchannel in fluidic communication with the first chamber and on an opposite side of the first chamber from the first microchannel. According to any one or more aspects disclosed herein, the first microchannel can be lined with blood vessel endothelial cells to mimic a blood vessel and the second microchannel can be lined with lymphatic endothelial cells to mimic a lymphatic vessel. According to any one or more aspects disclosed herein, the body can define further a second chamber in fluidic communication with and between the first chamber and the second microchannel. According to any one or more aspects disclosed herein, the second chamber can be filled with the matrix and predominantly T lymphocytes and the first chamber is filled predominantly with the B lymphocytes. According to any one or more aspects disclosed herein, the first microchannel and the first chamber can be circular.

According to further aspects of the present disclosure, a microfluidic device is disclosed. The device includes a body defining a first microchannel, a second microchannel, and at least one chamber. The first microchannel and the second microchannel have inlets and outlets to an exterior of the body, with the at least one chamber being in fluidic communication with the first microchannel and the second microchannel. The device further includes a matrix filling at least a portion of the first chamber, with the matrix being formed of a hydrogel. The matrix includes T lymphocytes, B lymphocytes, and optionally a reticular network configured to facilitate lymphocyte scanning by one or more of the T lymphocytes or B lymphocytes. In some embodiments, the device further includes a first membrane separating the first chamber from the first microchannel, and optionally a second membrane separating the first chamber from the second microchannel. In some embodiments, the device further includes endothelial cells (e.g., blood vessel endothelial cells) that are affixed to the first and/or second membranes (said affixing optionally further comprising one or more additional layers).

According to any one or more aspects disclosed herein, the device can include a second chamber of the at least one chamber in fluidic communication with the first chamber, the second chamber including tumor cells. According to any one or more aspects disclosed herein, the device can include a third membrane separating the first chamber from the second chamber and being formed of lymphatic endothelial cells. According to any one or more aspects disclosed herein, the first microchannel can be lined with lymphatic endothelial cells to mimic a lymphatic vessel and the second microchannel can be lined with blood vessel endothelial cells to mimic a blood vessel. According to any one or more aspects disclosed herein, the B lymphocytes can form clusters that mimic germinal centers within human lymph nodes.

According to further aspects of the present disclosure, a method is disclosed that includes providing a microfluidic device having a body having a microchannel in fluidic communication with a chamber, where the microchannel includes a microchannel inlet and a microchannel outlet, and the chamber includes a matrix. The method further includes providing said matrix with T lymphocytes and B lymphocytes. The method further includes culturing said T lymphocytes and B lymphocytes under conditions such that the B lymphocytes form clusters within the matrix.

According to any one or more aspects disclosed herein, the microchannel inlet, the microchannel, and the microchannel outlet can collectively define a fluid path, and said fluid path can be used to seed the matrix in step b) with the T lymphocytes and the B lymphocytes. According to any one or more aspects disclosed herein, the matrix can be an extracellular matrix. According to any one or more aspects disclosed herein, the extracellular matrix can be or include a hydrogel. According to any one or more aspects disclosed herein, said T lymphocytes and B lymphocytes can be seeded into the matrix by flowing PBMCs through the fluid path. According to any one or more aspects disclosed herein, the T and B lymphocytes can be seeded within the matrix in a ratio of about 40:60 to about 60:40 T lymphocytes to B lymphocytes. According to any one or more aspects disclosed herein, the density of the T and B lymphocytes within the matrix can be greater than 500,000 cells per milliliter. According to any one or more aspects disclosed herein, the density of the T and B lymphocytes within the matrix can be about $1\times10^{\wedge}8$ to about $2\times10^{\wedge}8$ cells per milliliter. According to any one or more aspects disclosed herein, the density of cells in the matrix can be such that the B lymphocytes self-organize into clusters.

According to any one or more aspects disclosed herein, the method further includes the step of d) measuring lymphocyte proliferation and/or antigen specificity. According to any one or more aspects disclosed herein, the method further includes the step of d) measuring lymphocyte cytokine and/or antibody secretion. According to any one or more aspects disclosed herein, the method further includes the step of d) exposing said lymphocytes to an agent. According to any one or more aspects disclosed herein, said agent can be selected from the group consisting of a cytokine, an antigen, and a drug. According to any one or more aspects disclosed herein, said agent can be selected from the group consisting of tumor antigens, pathogens, and vaccines. According to any one or more aspects disclosed herein, said agent can be selected from the group consisting of candidate drugs, known anti-cancer drugs, known checkpoint inhibitors, and candidate checkpoint inhibitors. According to any one or more aspects disclosed herein, the checkpoint inhibitor can be an antibody. According to any one or more aspects disclosed herein, said antibody can bind the PD-1 receptor on T cells. According to any one or more aspects disclosed herein, said matrix can include said agent and said agent can be released from the matrix. According to any one or more aspects disclosed herein, said matrix releases scaffolds comprising said agent. According to any one or more aspects disclosed herein, said released scaffolds can include microbeads. According to any one or more aspects disclosed herein, said released scaffolds can include nanoparticles. According to any one or more aspects disclosed herein, said nanoparticles can release bioactive molecules. According to any one or more aspects disclosed herein, the method further can include the step of seeding the matrix with additional immune and/or stromal cells. According to any one or more aspects disclosed herein, the method further can include the step of flowing additional immune and/or stromal cells into the device. According to any one or more aspects disclosed herein, said additional immune and/or stromal cells can form a reticular network within the matrix. According to any one or more aspects disclosed herein, the immune and/or stromal cells can be selected from the group consisting of monocytes, macrophages, and dendritic cells. According to any one or more aspects disclosed herein, the monocytes can be CD14+. According to any one or more aspects disclosed herein, the monocytes can be GM-CSF/IL-4 cultured monocytes. According to any one or more aspects disclosed herein, the reticular network can be an antigen presenting network. According to any one or more aspects disclosed herein, macrophages and dendritic cells can be monocyte-derived. According to any one or more aspects disclosed herein, said macrophages or dendritic cells can carry or present an antigen or portion thereof. According to any one or more aspects disclosed herein, said antigen or portion thereof can generate an immune response as measured by lymphocyte proliferation. According to any one or more aspects disclosed herein, said antigen or portion thereof can generate an immune response as measured by lymphocyte secretion of cytokines or secretion of antibody. According to any one or more aspects disclosed herein, said B lymphocyte clusters can contain less than 10% T lymphocytes. According to any one or more aspects disclosed herein, said B lymphocytes clusters can contain less than 5% T lymphocytes. According to any one or more aspects disclosed herein, said B lymphocytes clusters can contain less than 1% T lymphocytes. According to any one or more aspects disclosed herein, said culturing of step c) includes perfusing said lymphocytes with culture media at a flow rate. According to any one or more aspects disclosed herein, the method can further include the step of d) removing a portion of said culture media from set microchannel outlet or from said chamber. According to any one or more aspects disclosed herein, the method can further include the step of e) testing said culture media for secreted molecules. According to any one or more aspects disclosed herein, the method can further including the step of e) introducing said portion of said culture media into a different microfluidic device, said different microfluidic device comprising cells.

According to one or more additional aspects, a method is disclosed that includes providing a microfluidic device including a body having a microchannel in fluidic communication with a chamber, where the microchannel includes a microchannel inlet and a microchannel outlet, and the chamber includes a matrix. The method further includes providing said matrix with T lymphocytes and B lymphocytes, either before or after having the matrix within the chamber. The method further includes culturing the T lymphocytes and the B lymphocytes under conditions such that the B lymphocytes form clusters within the matrix, and exposing said lymphocytes to tumor cells.

According to any one or more aspects disclosed herein, said exposing of step d) can include introducing tumor cells into said device. According to any one or more aspects disclosed herein, said exposing of step d) can include removing at least a portion of said lymphocytes from said device and exposing said removed cells to tumor cells outside said device. According to any one or more aspects disclosed herein, the microchannel inlet, the microchannel, and the microchannel outlet collectively define a fluid path, and wherein said fluid path is used to seed the matrix in step b). According to any one or more aspects disclosed herein, the method can further include the step of e) measuring lymphocyte proliferation. According to any one or more aspects disclosed herein, the method can further include the step of e) measuring lymphocyte cytokine secretion and/or antibody secretion. According to any one or more aspects disclosed herein, the method can further include the step of e) exposing said lymphocytes to an agent. According to any one or more aspects disclosed herein, said agent can be selected from the group consisting of a cytokine, an antigen and a drug. According to any one or more aspects disclosed herein, said agent can be selected from the group consisting of tumor antigens, pathogens, and vaccines. According to any one or more aspects disclosed herein, said agent can be selected from the group consisting of candidate drugs, known anti-cancer drugs, known checkpoint inhibitors and candidate checkpoint inhibitors. According to any one or more aspects disclosed herein, the checkpoint inhibitor can be an antibody. According to any one or more aspects disclosed herein, said antibody can bind the PD-1 receptor on T cells. According to any one or more aspects disclosed herein, said antibody can bind the PD-L1 ligand on the tumor cells. According to any one or more aspects disclosed herein, the method further can include the step of f) detecting the impact of the agent on the lymphocytes. According to any one or more aspects disclosed herein, said detecting can include detecting tumor cell death by said lymphocytes.

According to further aspects of the present disclosure, a microfluidic device is disclosed. The device includes a body defining a first microchannel, a second microchannel, and at least a first chamber and a second chamber. The first microchannel and the second microchannel have inlets and outlets to an exterior of the body. Further, the first chamber is in fluidic communication with the first microchannel, and the second chamber is in fluidic communication with the second microchannel. The device further includes a matrix filling at least a portion of the first chamber, with the matrix being formed of a hydrogel. The matrix includes T lymphocytes, optionally B lymphocytes, and optionally a reticular network configured to facilitate lymphocyte scanning by one or more of the T lymphocytes or B lymphocytes. In some embodiments, the first chamber and the second chamber are in fluidic communication. In some embodiments, the first chamber and second chamber are in fluidic communication by means of a third chamber. In some embodiments, the device further includes a first membrane separating the first chamber from the first microchannel, and optionally a second membrane separating the first chamber from the second microchannel. In some embodiments, the device further includes endothelial cells (e.g., blood vessel endothelial cells) that are affixed to the first and/or second membranes (said affixing optionally further comprising one or more additional layers).

Additional aspects of the invention will be apparent to those of ordinary skill in the art in view of the detailed description of various embodiments, which is made with reference to the drawings, a brief description of which is provided below.

Figure 1:
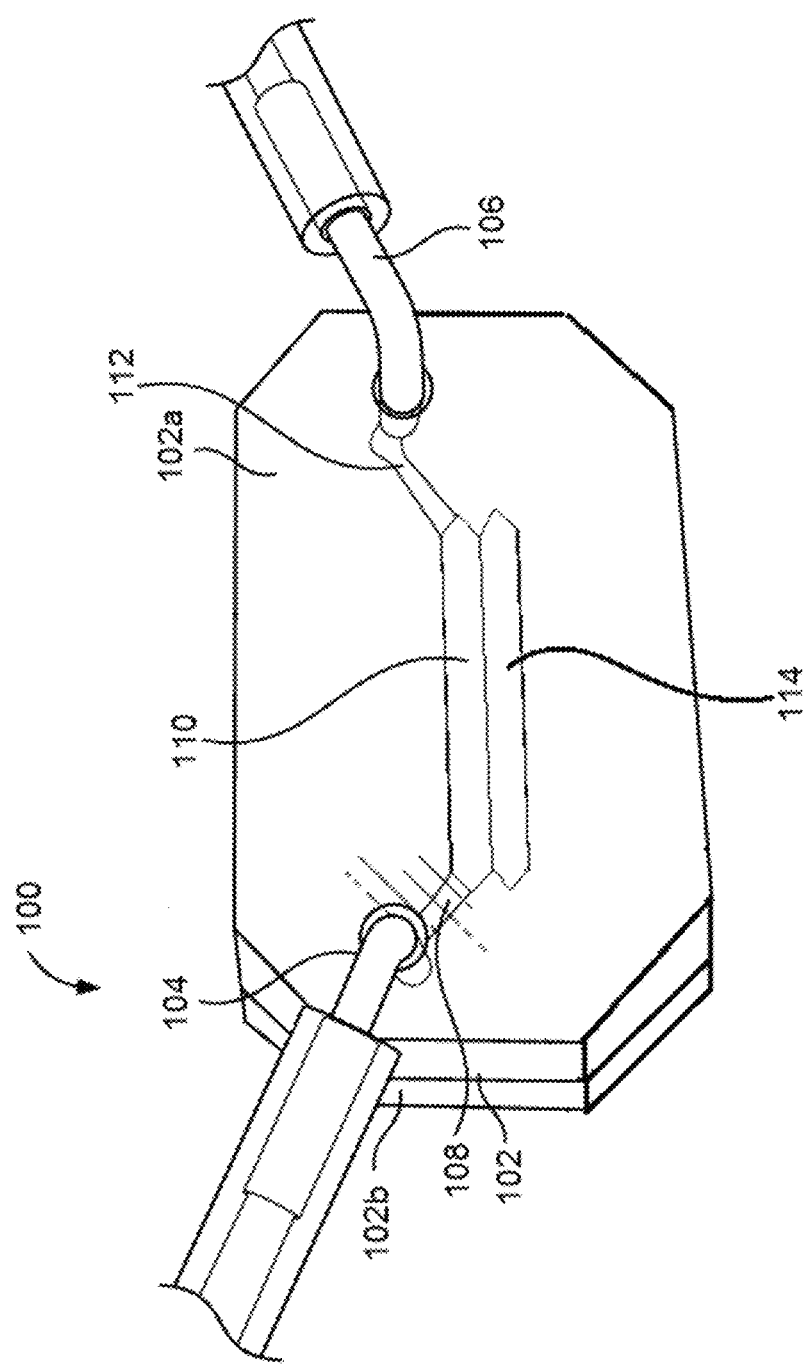
FIG. 1 illustrates a perspective view of an exemplary lymph or lymphoid organ-on-chip device ("OOC") microfluidic device, in accord with aspects of the present disclosure.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspects of the invention to the embodiments illustrated.

As used herein, the phrases "linked," "connected to," "coupled to," "in contact with," and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

As used herein, the term "channels" are pathways (whether straight, curved, single, multiple, in a network, etc.) through a medium (e.g., silicon, plastic, etc.) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents.

As used herein, the term "microchannels" is used to describe channels with at least some dimensions less than 1 millimeter and greater than 1 micron. Additionally, the term "microfluidic" as used herein relates to components where moving fluid is constrained in or directed through one or more channels, wherein one or more dimensions are 1 mm or smaller (microscale). Microfluidic channels may be larger than microscale in one or more directions, though the channel(s) will be on the microscale in at least one direction. In some instances, the geometry of a microfluidic channel may be configured to control the fluid flow rate through the channel (e.g., increase channel height to reduce shear). Microfluidic channels can be formed of various geometries to facilitate a wide range of flow rates through the channels.

The present invention contemplates a variety of "microfluidic devices," including but not limited to microfluidic chips (such as that shown in FIGS. 1-4). Such devices can contain gels and/or a matrix. The gel and/or matrix can include cells. In one embodiment, the present invention contemplates a microfluidic device comprising a body defining a first microchannel and a first chamber, the first microchannel having an inlet and an outlet to an exterior of the body, and the first chamber being in fluidic communication with the first microchannel, and a matrix filling (or at least partially filling) the first chamber.

U.S. Pat. No. 8,647,861, hereby incorporated by reference, describes microfluidic "organ-on-chip" devices comprising living cells on membranes in microchannels exposed to culture fluid at a flow rate. In contrast to static 2D culture, microchannels allow the perfusion of cell culture medium throughout the cell culture during in vitro studies and as such offer a more in vivo-like physical environment. In simple terms, an inlet port allows injection of cell culture medium into a cell-laden microfluidic channel or chamber, thus delivering nutrients and oxygen to cells. An outlet port then permits the exit of remaining medium as well as harmful metabolic by-products. In one embodiment, one or more microchannels connect to a chamber. In one embodiment, the membrane permits fluid and solids to pass between the first microchannel and the chamber.

The functionality of lymphoid cells and lymphoid tissues is implemented in one or more microfluidic devices or "chips" that enables the study of these cells and tissues in vitro, while mimicking at least some function of either of these tissues or their response to the stimuli and environment that the cells and tissue are exposed to in vivo. The ability to implement these microfluidic devices alone or as interconnected components that can simulate groups of organs or tissue systems is also disclosed. Optionally, the microfluidic devices can be inserted and removed from an underlying fluidic system that connects to these devices in order to vary the simulated in vivo conditions and organ systems.

The lymph in vivo interacts with other tissue and organ types, playing an important role in the adaptive immune system. In turn, the organ-on-chip lymph node and lymphoid system can be used to explore, model, and/or study the interaction of the lymph system with other elements of the in vivo system. Accordingly, the on-chip lymph node may be linked to one or more other tissue-culture systems, organomimetic systems, or organs-on-chips. Such linking may involve fluidically coupling the inputs, outputs, or both inputs and outputs of the lymph organ-on-chip to one or more of the systems. Such fluidic coupling may include, for example, tubing, and/or microfluidic channels, as well as discrete fluid transfers, e.g., by means of liquid-handling automation. Such fluidic coupling may optionally further include one or more mediators, which may be selected from the list including cells (e.g., dendritic cells, T cells, macrophages) and blood or blood components.

Although the present disclosure makes reference to human biology, human in vivo and the human lymphatic system, the disclosed aspects apply also to non-human species, including other mammals (e.g., mouse, rat, dog, monkey, and non-human primate)

FIG. 1 illustrates a perspective view of an exemplary OOC 100, in accord with aspects of the present disclosure. The OOC 100 includes a body 102. In some aspects, the body 102 can be formed of a single, monolithic structure. Alternatively, the body 102 can be formed of an upper body segment 102a and a lower body segment 102b. The body 102, including the upper body segment 102a and the lower body segment 102b, can be made of a polymeric material, such as polydimethysyloxane (PDMS), poly(methyl methacrylate) (PMMA), polycarbonate, cyclic olefin copolymer (COP), cyclic olefin polymer (COC), polyurethane, styrene-butadiene-styrene (SBS) and/or poly(styrene-ethylene/butylene-styrene) (SEBS) block copolymers, etc. By being formed of a clear material, such as PDMS, the OOC 100 permits the viewing of substances (e.g., fluids, media, particulates, etc.) within the OOC 100. Various image-gathering techniques, such as spectroscopy and microscopy, can be used to quantify and evaluate the effects of the fluid flow in the microchannel 110, as well as cellular behavior and cellular communication.

The body 102 (or upper body segment 102a) includes a fluid inlet 104 and a fluid outlet 106 that are in fluidic communication with a channel inlet 108, a microchannel 110, and a channel outlet 112. The combination of the fluid inlet 104, the channel inlet 108, the microchannel 110, the channel outlet 112, and the fluid outlet 106 define a first fluid path within the OOC 100, which allows fluids and solids (e.g., proteins, cells, drugs, agents, antigens, blood, viruses, bacteria, etc.) to flow through the OOC 100.

As further discussed below, the OOC 100 can, alternatively, include more than one fluid path by including one or more additional fluid inlets, channel inlets, microchannels, channel outlets, and/or fluid outlets. Where the body 102 is formed of a lower body segment 102b, for example, the lower body segment 102b can include a second fluid path, similar to the first fluid path in the upper body segment 102a. Further, the multiple fluid paths can have interfaces with each other that allow material (e.g., elements, molecules, proteins, cells, drugs, agents, antigens, blood, viruses, bacteria, etc.) to pass between the different fluid paths. In some aspects, a layer or a surface, such as a membrane, a pillar structure, a surface of a matrix (e.g., hydrogel), etc., can define a boundary of the fluid paths at the interfaces.

Although referred to herein as a fluid inlet (e.g., fluid inlet 104) and a fluid outlet (e.g., fluid outlet 106), according to a preferred embodiment, the fluid inlet and the fluid outlet can be both an inlet and an outlet, such as in the case of bi-directional flow of fluid through the microchannel (e.g., microchannel 110). By way of example, and without limitation, fluid can flow into the fluid inlet 104 and then flow out of the fluid outlet 106. Alternatively, or subsequently, the fluid can flow into the fluid outlet 106 and then flow out of the fluid inlet 104. Thus, the terms inlet and outlet are used for purposes of convenience and should not be interpreted as limiting.

The OOC 100 also includes a chamber 114 within the body 102. The chamber 114 is in fluidic communication with the microchannel 110 (e.g., the first fluid path) either directly (e.g., no membrane, matrix, or other layer or surface separating the chamber 114 and the fluid path) or indirectly (e.g., a membrane, pillar structure, matrix, matrix surface, or other layer or surface exists and defines a boundary between the chamber 114 and the fluid path). In some aspects, and as further discussed below, the OOC 100 can have more than one chamber 114, with each chamber in direct or indirect fluidic communication with one or more, or all, of the fluid paths and chambers within the OOC 100. In some embodiments, both the microchannel 110 and the chamber 114 can be formed to be about 150 to about 250 mm long and about 1 mm wide. In some embodiments, the chamber 114 can have a length ranging between 2 mm and 100 mm, and a width ranging between 50 μm and 20 mm.

The OOC 100 is configured to simulate a biological function that typically includes cellular communication as would be experienced in vivo within organs, tissues, cells, etc. Depending on the application, interfaces between one or more fluid paths and/or chambers permit the migration of elements, molecules, proteins, cells, drugs, agents, antigens, blood and blood components, viruses, bacteria, particulates, media, etc. there between. For example, where a membrane and/or matrix defines an interface between two chambers and/or a chamber and a fluid path and/or microchannel, the membrane and/or matrix can be designed to have a porosity (or other structure that permits permeation) to allow migration of the substances.

The OOC 100 can be seeded by various fluids and solids to create cell layers on the interior surfaces of, for example, the microchannel 110 and chamber 114. The microchannel 110 and chamber 114 lined with one or more cell layers mimics portions of a human body in vivo. By way of example, and without limitation, the cell layers can include endothelial cells, including but not limited to vascular endothelial cells, lymphatic endothelial cells, or other lymphatic tissue cells. By way of example, the cells can include human dermal lymphatic endothelial cells and umbilical vein endothelial cells (HUVEC). In some embodiments, the cells layers may coat at least a portion of a membrane or matrix surface, e.g., a membrane or matrix surface separating a microchannel from a chamber.

Figure 2A:
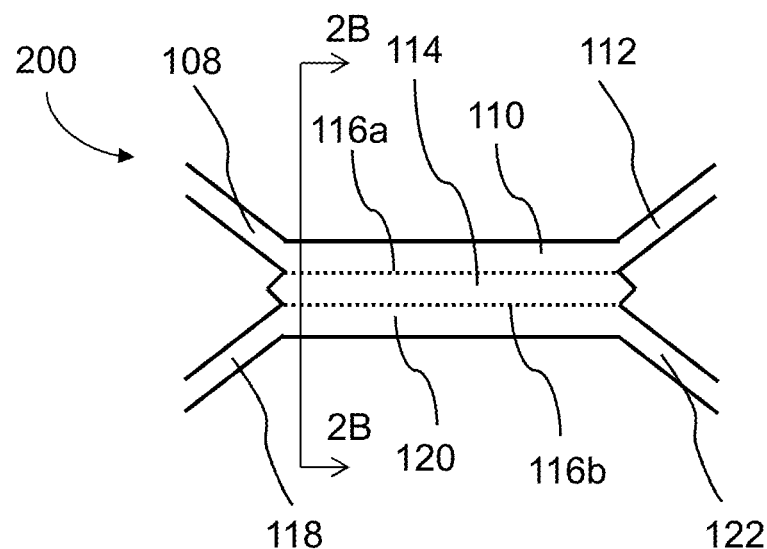
FIG. 2A illustrates a schematic view of another microfluidic device, in accord with aspects of the present concepts.
Figure 2B:
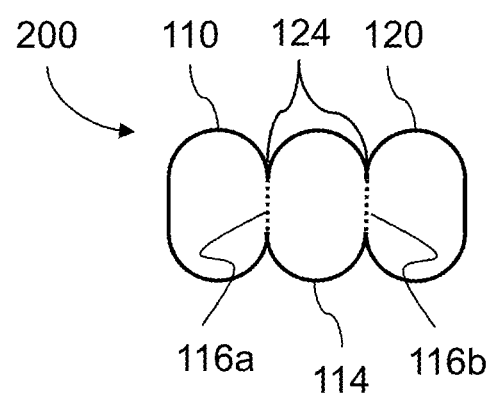
FIG. 2B illustrates a cross-sectional view of the device of FIG. 2A along the line 2A-2A, in accord with aspects of the present disclosure.

FIG. 2A illustrates a schematic view of another exemplary OOC 200, in accord with aspects of the present disclosure. FIG. 2B illustrates a cross-section of the OOC 200 along the line 2B-2B in FIG. 2A. The OOC 200 is similar to the OOC 100; thus, similar features are labeled using the same element numbers and are described above. However, the OOC 200 includes a second fluid path. The body (not shown) of the OOC 200 includes a fluid inlet (not shown), similar to the fluid inlet 104, and a fluid outlet (not shown), similar to the fluid outlet 106, which are in fluidic communication with a channel inlet 118, a microchannel 120, and a channel outlet 122. The channel inlet 118, the microchannel 120, and the channel outlet 122 define, in combination with the fluid inlets and outlets, the second fluid path.

Between the first fluid path (e.g., channel inlet 108, microchannel 110, and channel outlet 112) and the second fluid path (e.g., channel inlet 118, microchannel 120, and channel outlet 122) is the chamber 114. The first and second fluid paths allow for fluid flow within the OOC 200 and perfusion of material (e.g., (e.g., elements, molecules, proteins, cells, viruses, bacteria, etc.) into the chamber. In particular, the first and second fluid paths permit the flow of fluids and solids either in the same direction or in opposition directions. As explained further below, the microchannels 110 and 120 can be used to culture vascular endothelium (e.g., lymphatic and/or blood) on the exposed sides of the chamber 114.

The microchannel 110 and the chamber 114 can be separated by a constriction 124 in the body. The constriction 124 is a reduction of the longitudinal cross-sections of the microchannel 110 and the chamber 114 as compared to, for example, the largest longitudinal cross-section or the average longitudinal cross-section of the microchannel 110 and the chamber 114. Thus, the construction 124 reduces interface area between the microchannel 110 and the chamber 114. Alternatively, or in addition, the microchannel 110 and the chamber 114 can be separated by a membrane, pillar structure, or surface of a matrix filling the chamber 114, as represented by the dotted line 116a. Similarly, the chamber 114 and the microchannel 120 can be separated by the constriction 124 in the body, a membrane, pillar structure, or surface of a matrix filling the chamber 114, represented by the dotted line 116b, or a combination thereof. Based on ability to flow fluids and solids past the chamber 114, and perfuse into the chamber, the OOC 200 can be configured to mimic portions of the lymphatic system, such as a lymph node, where the chamber 114 mimics the lymph node and the first and second fluid paths mimic blood vessels and/or lymphatic vessels supplying material to the lymph node. For example, the OOC 200 permits the co-culture of endothelial cells (e.g., human dermal lymphatic endothelial cells and/or umbilical vein endothelial cells (HUVEC)) to form adjacent to the chamber 114 by perfusion on both sides of the chamber 114. In some embodiments, said endothelial cells are cultured on the membrane, pillar structure, or matrix surfaces represented by 116a and/or 116b. For the avoidance of doubt, endothelial cells may be cultured on either side or both sides of said membrane or surface. In a particular embodiment, endothelial cells are seeded onto surface 116a or 116b by perfusion on one or both sides of the chamber 114, e.g. by flowing said cells into microchannel 110 and/or microchannel 120.

Figure 3A:
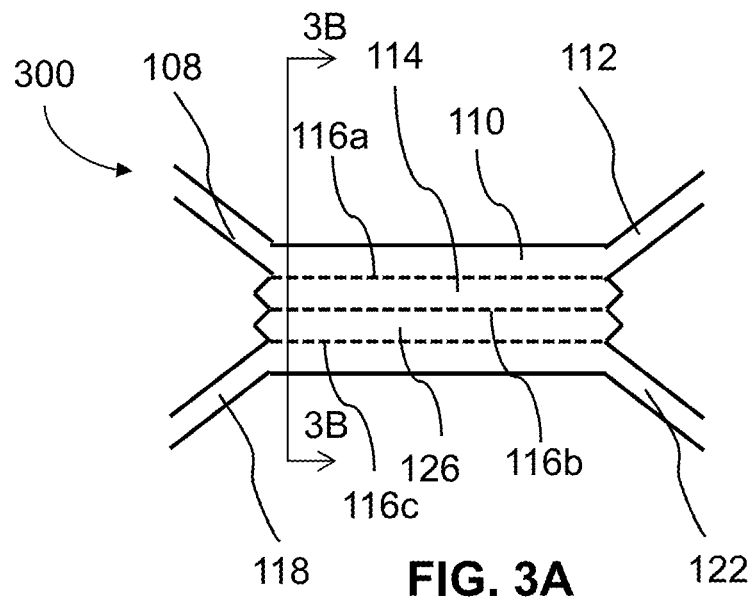
FIG. 3A illustrates a schematic view of another microfluidic device, in accord with aspects of the present disclosure.
Figure 3B:
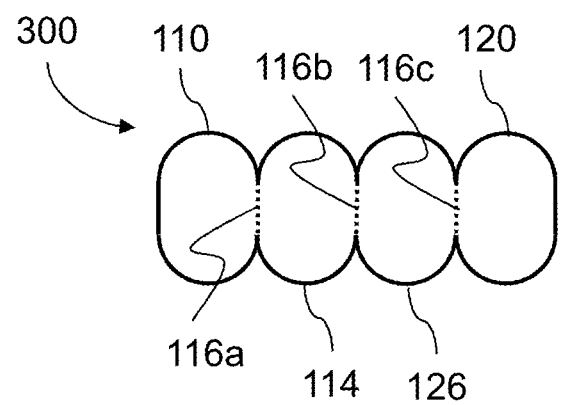
FIG. 3B illustrates a cross-sectional view of the device of FIG. 3A along the line 3A-3A, in accord with aspects of the present disclosure.

FIG. 3A illustrates a schematic view of another exemplary OOC 300, in accord with aspects of the present disclosure. FIG. 3B illustrates a cross-section of the OOC 300 along the line 3B-3B in FIG. 3A. The OOC 300 is similar to the OOCs 100 and 200; thus, similar features are labeled using the same element numbers and are described above. However, the OOC 300 includes two chambers, i.e., chamber 114 and chamber 126. The different chambers 114 and 126 can be configured to mimic different portions of the human lymphatic system, as described further below. For example, the chamber 114 can be configured to mimic a lymph node, and the chamber 126 can be configured to mimic a tumor, such as by seeding the chamber 126 with tumor cells.

In some embodiments, the devices of FIGS. 1-3 can be manufactured using a layered approach. For example, in a particular embodiment in line with FIG. 2, the microchannel 110 is disposed in a top substrate, this top substrate laminated to a first membrane (represented by 116a), in turn laminated to a second substrate comprising the chamber 114. In this example, the second substrate is optionally further laminated to a second membrane (represented by 116b), which in turn is laminated to a bottom substrate comprising the microchannel 120.

Figure 4:
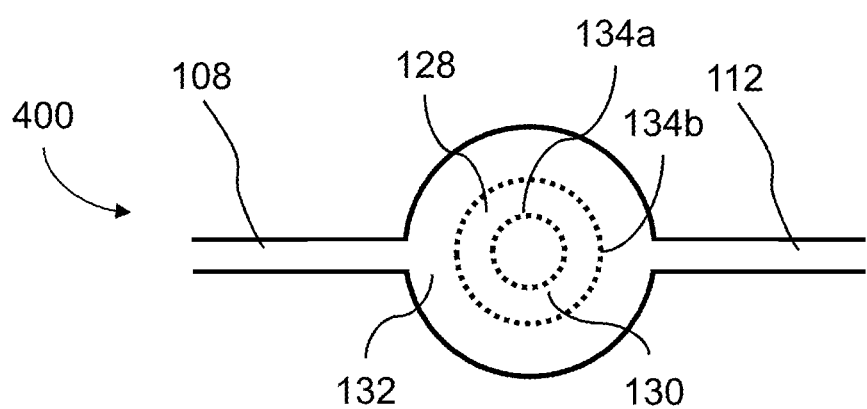
FIG. 4 illustrates a schematic view of another microfluidic device, in accord with aspects of the present disclosure.

FIG. 4 illustrates a schematic view of another exemplary OOC 400, in accord with aspects of the present disclosure. Rather than including a linear chamber, the OOC 400 can include one or more circular chambers 128 and 130 that lie within the center of a circular microchannel 132. The circular microchannel 132 and circular chambers 128 and 130 can be separated by pillar arrays or membranes 134a and 134b. The pillar arrays or membranes 134a and 134b can be formed within the circular microchannel 132, or formed outside of the microchannel 132 and later placed within the microchannel 132, and define the chambers 128 and 130 within the circular microchannel 132. The circular microchannel 132 and the chambers 128 and 130 provide the ability to mimic compartmentalization and/or radial gradients that can occur in the human lymphatic system. In particular, the chambers 128 and 130 can be viewed in analogy with the chambers 114 and 126 of FIG. 3.

FIGS. 1-4 describe specific types of OOCs that can be used in forming a human lymphoid tissue-on-chip, depending on the specific functionality desired. However, aspects of the present invention can be applied to various other types of devices without departing from the spirit and scope of the present disclosure. By way of example, the present concepts disclosed herein can apply to any microfluidic device (or a plurality of microfluidic devices), and not only the geometry of the microfluidic devices disclosed herein. For example, although FIG. 2A illustrates the channels being lateral to each other, aspects of the present disclosure include and cover a very important embodiment would involve a vertical design.

To form the human lymphoid tissue-on-chip, one or more of the chambers (e.g., chamber 114 and/or chamber 126 are prepared to mimic a human lymph node or human lymphoid tissue. The fluid paths of the chips are used to seed the chambers with the fluid and material to form a human lymphoid tissue-on-chip, as described in detail below. Although described below primarily with respect to the OOC 200, such a description is merely for convenience and should not be interpreted as limiting.

Figure 5A:
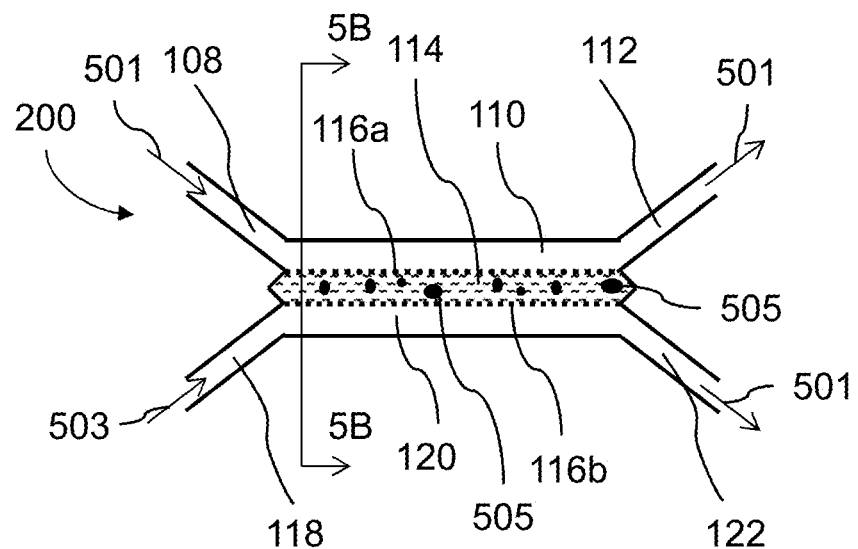
FIG. 5A illustrates a schematic view of the device of FIG. 2A seeded to be configured as a human lymphoid tissue-on-chip or organ-on-chip, in accord with aspects of the present disclosure.
Figure 5B:
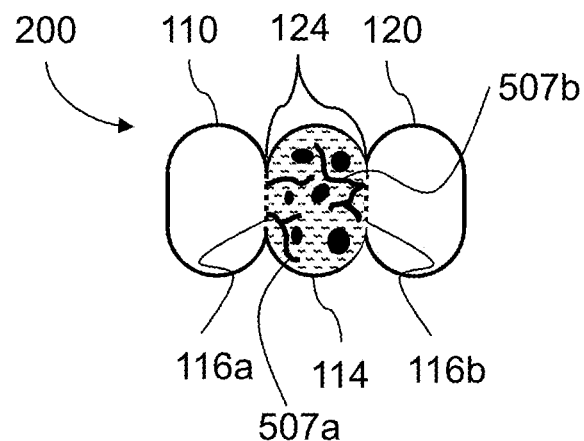
FIG. 5B illustrates a cross-sectional view of the device of FIG. 5A along the line 5A-5A, in accord with aspects of the present disclosure.

FIG. 5A illustrates a schematic view of the OOC 200 configured as a human lymphoid tissue-on-chip, in accord with aspects of the present disclosure. Further, FIG. 5B illustrates a cross-sectional view of the OOC 200 along the line 5B-5B in FIG. 5A. Initially, the arrows 501 represent the ability to flow fluids and solids within the first fluid path defined, at least in part, by the channel inlet 108, the microchannel 110, and the channel outlet 112. Similarly, the arrows 503 represent the ability to flow fluids and solids within the second fluid path defined, at least in part, by the channel inlet 118, the microchannel 120, and the channel outlet 122. The membrane, pillar structure, or surface of a matrix 116a separates the first fluid path 501 from the chamber 114, and the membrane, pillar structure, or surface of a matrix 116b separates the second fluid path 503 from the chamber 114, both of which are discussed in greater detail below. However, in one or more aspects, the OOC 200 can omit any membranes 116a and 116b. For example, referring to FIG. 5B, in addition to the membranes 116a and 116b, the microchannels 110 and 120 can be separated, at least in part, from the chamber 114 by constrictions 124. However, in some aspects, any membranes 116a and 116b can be omitted and the OOC 200 may have only the constrictions 124, thus enabling direct cell-cell contact between cells in the microchannels 110 and 120 and cells in the chamber 114, rather than indirect contact through one or both of the boundaries 116a and 116b.

The first and second fluid paths can be used to flow different types of cells, such as blood and lymphatic endothelial cells, or blood cells (including T-cells, B-cells, macrophages, and dendritic cells), flow tissue culture media, blood or blood components, and/or introduce agents (e.g. drugs, antigens, cytokines) through the OOC 200 and/or perfuse into the chamber 114. Alternatively, in some aspects, the first and second fluid paths can be used to flow the same type of cells through the OOC 200 and/or perfused into the chamber 114. Thus, a combination of lymphatic and vascular endothelium can be used. In one or more aspects, the membrane or interface 116a can support lymphatic endothelial cells to have the first fluid path mimic a lymphatic vessel. Lymphatic endothelial cells also can line the interior walls of the channel inlet 108, the microchannel 110, and the channel outlet 112. The lymphatic endothelial cells can line the first fluid path by flowing lymphatic endothelial cells through the first fluid path. The membrane 116b can support blood vessel endothelial cells to have the second fluid path mimic a blood vessel. Blood vessel endothelial cells also can line the interior walls of the channel inlet 118, the microchannel 120, and the channel outlet 122. The blood vessel endothelial cells can line the second fluid path by flowing blood vessel endothelial cells through the first fluid path. The membranes 116a and 116b (and any membrane discussed herein) can be made of a material having a plurality of pores or apertures therethrough, whereby molecules, cells, fluid or any media is capable of passing through the membranes 116a and 116b via the one or more pores. It is contemplated that the membranes 116a and 116b can be made of a material that allows the membranes 116a and 116b to undergo stress and/or strain in response to pressure differentials present within the OOC 200. Alternatively, the membranes 116a and 116b can be relatively inelastic, in which the membranes 116a and 116b undergo minimal or no movement while media is passed through one or more of the microchannels. In some aspects, the pores or apertures of the material that forms the membranes 116a and 116b can be about 0.4 to 10 μm in diameter. In some further aspects, the pores or apertures of the material that forms the membranes 116a and 116b can be about 0.4 to 1 μm in diameter.

The first and second fluid paths are used to fill and seed the chamber 114 with a matrix (represented by the dashed pattern). Alternatively, separate fluidic paths (not depicted) may be used to seed the chamber 114. The matrix is intended to act as the stroma of a lymph node or lymphoid tissue. Specifically, the matrix can be an extracellular matrix. In some aspects, the matrix can be formed of a hydrogel. More particularly, the matrix can be formed of, for example, MATRIGEL, collagen, fibrin, and/or alignate. With respect to MATRIGEL, MATRIGEL includes a fibrillar network of collagens, laminin, and heparin sulfate proteoglycan. In some aspects, the matrix can further include about 1.5 mg/ml of bovine collagen I to improve longevity of the matrix. The matrix can also include Roswell Park Memorial Institute (RPMI) medium. In some aspects, the matrix can include the MATRIGEL and the RPMI medium at about a 50 to 50 mix, and include the 1.5 mg/ml collagen I.

In some embodiments, the matrix is provided with T lymphocytes, B lymphocytes, or a combination thereof. In some aspects, the matrix can be provided with the T lymphocytes, the B lymphocytes, or a combination thereof by pre-mixing or pre-formulating the matrix with the T lymphocytes, B lymphocytes, or a combination thereof prior to at least partially filling the chamber 114 with the T lymphocytes, the B lymphocytes, or a combination thereof mixed in the matrix. Alternatively, or in addition, the matrix can be provided with the T lymphocytes, the B lymphocytes, or a combination thereof by seeding the T lymphocytes, the B lymphocytes, or a combination thereof within the matrix after the matrix has at least partially filled the chamber 114. The T lymphocytes and B lymphocytes can be formulated or seeded into the matrix by including PBMCs, where the PBMCs include the T lymphocytes and B lymphocytes.

Although PBMCs generally have 40-50% T lymphocytes and only 3-15% B lymphocytes, whole lymph nodes contain about 50-60% T lymphocytes and about 40-50% B lymphocytes. Thus, in some embodiments, the T and B lymphocytes can be provided within the matrix in a ratio of about 40:60 to about 60:40 T lymphocytes to B lymphocytes and, preferably, the ratio of T lymphocytes to B lymphocytes is about 60:40. In some embodiments, the density of the T and B lymphocytes within the matrix is seeded to be about $1 \times 10^8$ to about $2 \times 10^8$ cells per milliliter, but at least greater than 500,000 cells per milliliter.

Where the OOC includes multiple chambers, such as in the cases of FIGS. 3A, 3B, and 4 for the OOCs 300 and 400, each chamber can be provided with T lymphocytes, B lymphocytes, or a combination thereof. For example, in the device of FIG. 3, a matrix containing T lymphocytes (i.e., not B lymphocytes) can be provided in the chamber 114, and a matrix containing B lymphocytes (i.e., not T lymphocytes) can be provided in the chamber 126. Where chambers include only T or B lymphocytes, the densities of the lymphocytes can be about $1 \times 10^8$ to about $2 \times 10^8$ cells per milliliter to promote self-organization into clusters, such as for the B lymphocytes. For example, the density of the T lymphocytes in one chamber can be about $1 \times 10^8$ to about $2 \times 10^8$ cells per milliliter and the B lymphocytes in the other chamber can be about $1 \times 10^8$ to about $2 \times 10^8$ cells per milliliter. However, only one type of lymphocyte is within each chamber such that the ratio is 100:0 or 0:100 T lymphocyte to B lymphocyte.

Further variations exist between the case of having only one type of lymphocyte in each chamber of multiple chambers and having only one chamber with both T and B lymphocytes. For example, in some aspects, one chamber (e.g., chamber 114) can be predominately T lymphocytes but still include B lymphocytes, and the other chamber (e.g., chamber 126) can be predominately B lymphocytes but still include T lymphocytes. In the case of the OOC 300, the chamber 114 can be 60:40 T lymphocytes to B lymphocytes and the chamber 126 can be 40:60 T lymphocytes to B lymphocytes. At the above densities, the B lymphocytes self-organize into clusters within the OOC 200, as discussed below with respect to FIGS. 6A-6D and 7A-7C.

In some embodiments, the matrix also is formulated to include or is seeded to include several types of immune and stromal cells that form a reticular network within the matrix. In some aspects, the reticular network allows the T and B lymphocytes to can scan for antigen and costimulatory signals by providing a network of connective tissue and fibers. The reticular network allows lymphocytes to traffic from one cell to another looking for antigen and costimulatory signals. The immune and stromal cells that can be used to form the reticular network include, for example, monocytes (e.g., CD14+ obtained by magnetic bead selection before isolation of lymphocytes), monocyte-derived macrophages and dendritic cells (moDC), such as GM-CSF/IL-4 cultured monocytes. Other cells that can be used include, for example, macrophages and dendritic and stromal cells from human lymph nodes. By way of example, the monocytes and the monocyte-derived dendritic cells can be used to establish an antigen-presenting reticular network matrix for lymphocyte scanning. In some aspects, the matrix can include monocytes at a frequency of about 5 to 20%. The monocytes and/or monocyte-derived dendritic cells can be seeded within the chamber 114 through perfusion in one or both of the first and second fluid pathways to provide surfaces that enable lymphocyte trafficking and antigen recognition (for example, finding a pathogen protein to which the lymphocyte is reactive). Further, dendritic cells that carry an antigen (e.g., a protein, lipid, or pathogen that the body can mount an immune response to) can be delivered into the system to generate a successful immune response as defined by T and B lymphocyte proliferation and secretion of cytokines.

According to the above conditions, the B lymphocytes form clusters 505. The clusters 505 are sites within the matrix where the B lymphocytes aggregate, such that the density of the B lymphocytes increases in these areas of the matrix as compared to the previous generally uniform density of the B lymphocytes within the matrix. Specifically, the above conditions promote self-organization of B lymphocyte clusters 505. In some aspects, the T lymphocytes generally are excluded from the clusters 505, such as, for example, being less than 5% lymphocytes, less than 1% lymphocytes, or even less. In particular, while the B lymphocytes form into the clusters 505, the density of the T lymphocytes generally remains uniform, such as the uniformity prior of the T lymphocytes to the B lymphocytes forming the clusters 505. Although T lymphocytes may be found within the clusters 505 that form, it is the aggregation of the B lymphocytes that form the clusters 505. The B lymphocyte clusters 505 are similar to B lymphocyte follicles found in vivo. Further, the B lymphocyte clusters 505 can act as germinal centers. In particular, the clusters 505 of the B lymphocytes are sites where B lymphocytes can multiply, differentiate, and mutate their antibody genes (e.g., somatic hypermutation to achieve higher affinity), and switch the class of their antibodies during a normal immune response to an infection. Examples of the clusters are further shown in FIGS. 6A-6D and 7A-7C.

Figure 6A:
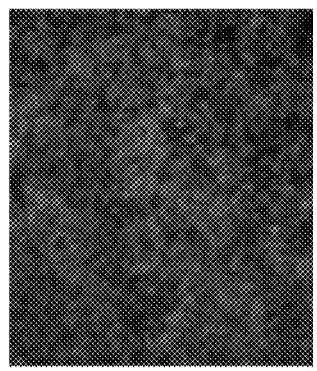
FIG. 6A illustrates a response of T lymphocytes during culturing within a microfluidic device, in accord with aspects of the present disclosure.
Figure 6B:
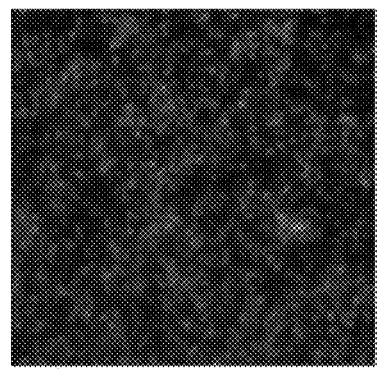
FIG. 6B illustrates a response of B lymphocytes during culturing within a microfluidic device, in accord with aspects of the present disclosure.
Figure 6C:
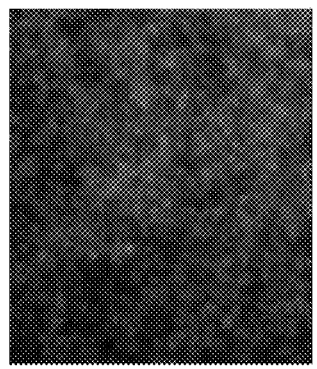
FIG. 6C illustrates a response of T lymphocytes during further culturing within a microfluidic device, in accord with aspects of the present disclosure.
Figure 6D:
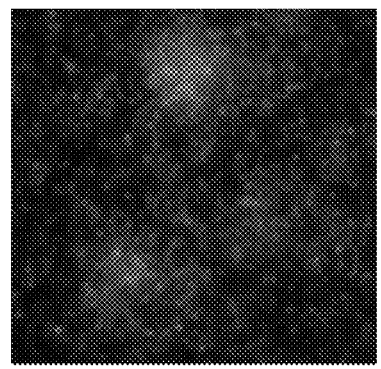
FIG. 6D illustrates a response of B lymphocytes during further culturing within a microfluidic device, in accord with aspects of the present disclosure.
Figure 6E:
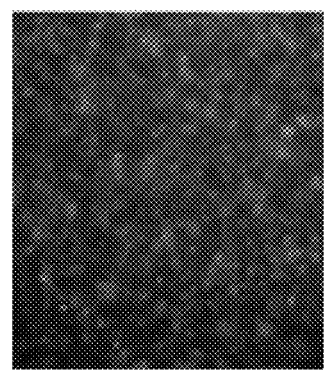
FIG. 6E illustrates a response of lymphocytes during culturing within a microfluidic device at lower density levels, in accord with aspects of the present disclosure.

Referring to FIG. 6A, FIG. 6A figure shows the T lymphocytes (represented by the lighter areas) in the matrix after one day of culturing. Similarly, FIG. 6B shows the B lymphocytes (represented by the lighter areas) in the matrix after one day of culturing. As shown, the distribution of the T and B lymphocytes (represented by the lighter areas) is generally uniform. In contrast, FIG. 6C shows the T lymphocytes (represented by the lighter areas) in the matrix after four days of culturing, and FIG. 6D shows the B lymphocytes (represented by the lighter areas) in the matrix after four days of culturing. Although the distribution of the T lymphocytes in FIG. 6C (represented by the lighter areas) is still generally uniform, the distribution of the B lymphocytes in FIG. 6D (represented by the lighter areas) is clustered, primarily at the top-center and bottom-left portions of the image. As evidence that a density of less than 500,000 cells per milliliter affects the self-organization of B lymphocytes clusters, FIG. 6E illustrates the results of T and B lymphocyte seeding at levels less than 500,000 cells per milliliter. Based on the uniformity of the light areas, there is no clustering of the T or B lymphocytes, unlike the conditions at least in FIG. 6D.

Figure 7A:
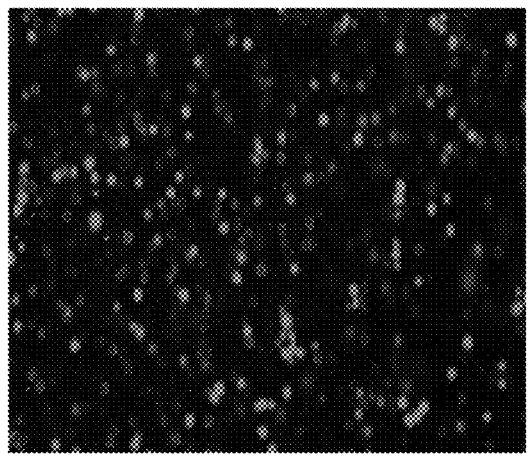
FIG. 7A illustrates a generally uniform distribution of the T and B lymphocytes, in accord with aspects of the present disclosure.
Figure 7B:
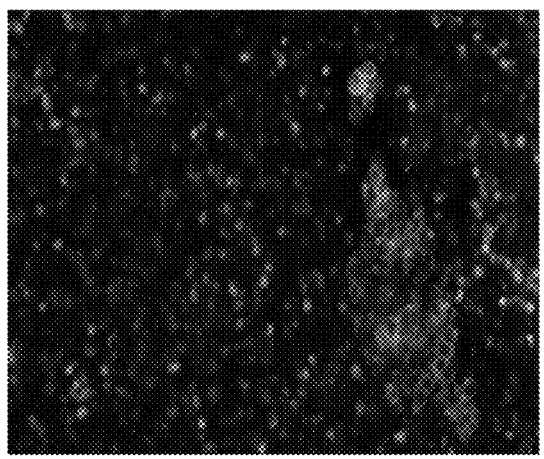
FIG. 7B illustrates clustering of the B lymphocytes, in accord with aspects of the present disclosure.
Figure 7C:
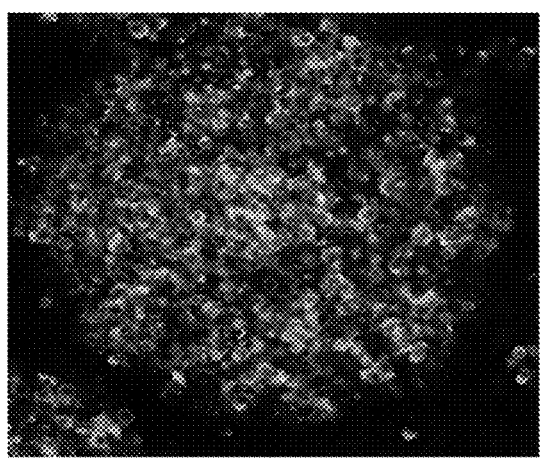
FIG. 7C illustrates production of T and B lymphocytes in response to an antigen, in accord with aspects of the present disclosure.

Similar phenomena occurred based on the polarization of cluster of differentiation 3 (CD3) and cytotoxic T-lymphocyte-associated protein 4 (CTLA-4) during four to seven days of culture within the OOC 200, where a significant fraction of T cells were polarized with CD3 and CTLA-4 accumulating in cap like structures. Referring to FIGS. 7A-7C, FIG. 7A shows a generally uniform distribution of the T and B lymphocytes at day zero, as represented by the light areas. At day 7, the T and B lymphocytes have organized into follicle like structures, where the T lymphocytes are CTLA-4 positive, as represented by the light areas in FIG. 7B. FIG. 7C shows the increase in size of the clusters of T and B lymphocytes after activation by exposure to SAC, as represented by the light areas. These results indicate that the tissue like density and matrix within the human lymphoid tissue-on-chip can recapitulate human lymphoid tissue polarization in vitro.

To mimic in vivo vasculature, the first and second fluid paths can be used to provide one or more culture mediums, blood, or blood components, to the chamber 114 to culture lymphatic or vascular endothelium on either side on the exposed surface of the matrix. The blood and lymphatic endothelium can be grown as a monolayer, such as to form the membrane 116a and 116b or as a vessel (tube) that has sprouted into many small capillaries. The culturing can further cause vessels 507a and 507b (FIG. 5B) to form inside the matrix based on the angiogenic factors produced by lymphocytes. As an example, the vessels 507a are lymphatic vessels from the first fluid path mimicking the lymphatic endothelium, and the vessels 507b are blood vessels from the second fluid path mimicking the blood vessel endothelium. The vessels 507a and 507b further provide a reticular network of supporting cells that facilitate 3D organization and lymphocyte "scanning," which allows lymphocytes to traffic from one cell to another looking for signals.

In some aspects, the matrix can contain release scaffolds that can be used to deliver agents within the matrix. For example, the release scaffolds can be microbeads and/or nanoparticles. The microbeads and/or nanoparticles can release chemokines or other bioactive molecules into the matrix. The release of these molecules can be controlled to create microdomains within the matrix. The microdomains can be used to promote 3D organization of the T and B lymphocytes, such as promoting the formation of B lymphocyte follicles. In some aspects, the microdomains can be used to create cytokine gradients within the matrix. The release scaffolds can be activated according to various techniques.

As configured above, the OOC 200 enables the real-time visualization of trafficking or extravasation across the lymphatic or blood vessel endothelium to the lymph node, as represented by the chamber 114, including the draining of molecular antigens (e.g., proteins, lipids), adjuvants (e.g., lipopolysaccharide (LPS) or CpG), whole pathogens (e.g., salmonella or human immunodeficiency virus (HIV)), and the active migration of mammalian cells (e.g., tumor cells, immune cells, such as dendritic cells, lymphocytes, etc.).

Although described above as using PBMCs to seed the chambers, cellular composition of PBMCs can vary. For example, different combinations of T and B lymphocytes from PBMCs can exist. The OOC 200 can be varied according to the variations in PBMCs by seeding the OOC 200 using the different PBMCs. In some aspects, the PBMCs used can be from donors or from patients with a specific ailment, such as melanoma or lymphoma patients. Further, the OOC 200 can be seeded with other cells and materials, such as monocytes from PBMCs, monocyte-derived dendritic cells, and monocyte-derived macrophages, etc. In some aspects, cells from human tonsils or other surgically resected lymph nodes can be used within the OOC 200. In some aspects, induced pluripotent stem (iPS) cells from individual patients also can be used to generate immune cells to place within the OOC 200 for personalized medicine. The above-described cells can be used from donor samples, or from patient samples for specific analysis tied to a specific patient. For example, the patient samples can be tied to specific cancer patients, HIV infected individuals, patients with other infectious diseases, patients with autoimmune diseases, etc. Further, the macrophages within the matrix can form subcapsular sinus macrophages, which can provide a layer of retained antigens for lymphocytes to access.

The other OOCs described herein allow for other variations depending on the specific aspects being tested. With respect to the OOC 300, as an example, an unfractionated tumor sample, including melanoma, immune infiltrate, and endothelial cells, can be within the chamber 126. As an example, biopsies of a tumor can be seeded into the chamber 126. The membrane 116b separating the chamber 114 and the chamber 116 can be a lymphatic monolayer. Further, the chamber 114 can be configured as described above as a human lymph node. Such a configuration allows for the study of the impact on lymph node morphology and trafficking of labeled cells from the lymph tissue in the chamber 114 to the cancer tissue in the chamber 126. Further, the impact on inhibitory receptors and the effect of blocking function on immune stimulation can also be studied. The ability to perform these studies can provide a basis for further iteration (tumor fractionation, labeling, etc.) to study melanoma micrometastases in the lymph node, the difference in response of tumor infiltrating lymphocytes and lymph node lymphocytes to therapy, and the construction of a lymph node draining a microfluidically connected tumor via a lymphatic vessel.

With the two fluid paths, and in some circumstances the single fluid path, one or more agents can be delivered and perfused to the human lymphoid tissue-on-chip. In some embodiments, said agents are selected from the list comprising a drug, a candidate drug, an immune activating stimuli, an antigens, a pathogen, a vaccine, and a checkpoint inhibitor. For example, *Staphylococcus aureus* cowan I (SAC) can be delivered by using a heat killed formalin fixed formulation of SAC. With such stimulation, T lymphocyte activation can be evidenced by the production of abundant levels of cytokine IL-2. The detection can occur by monitoring effluent of the human lymphoid tissue-on-chip from the first and/or second fluid paths. For example, the effluent from the human lymphoid tissue-on-chip can be run through an assay (e.g., enzyme-linked immunosorbent assay (ELISA)) for detection of the components within the chip effluent.

Figure 8:
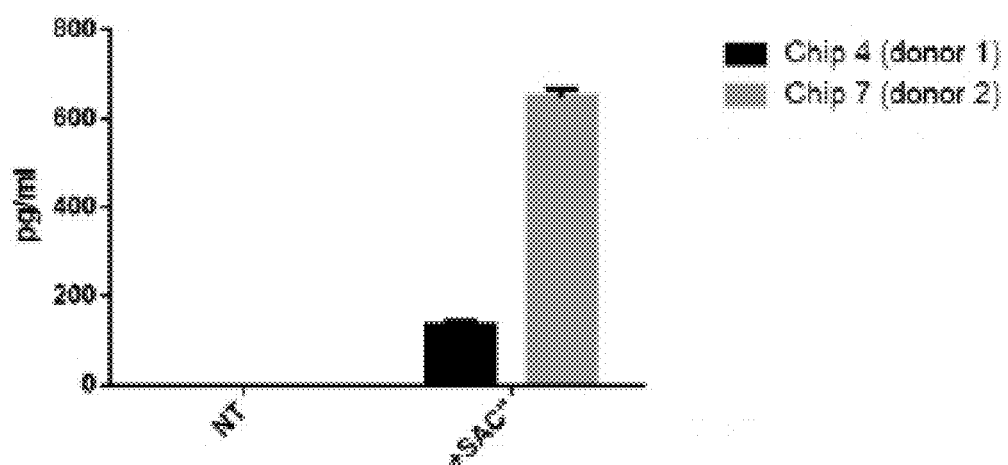
FIG. 8 shows a plot of cytokine IL-2 production in response to SAC activation for two human lymphoid tissue-on-chips, in accord with aspects of the present disclosure.

FIG. 8 shows a plot of cytokine IL-2 production in response to SAC activation for two human lymphoid tissue-on-chips, in accord with aspects of the present concepts. FIG. 8 shows that the human lymphoid tissue-on-chip according to the present disclosure has a response to the SAC activation by the production of cytokine IL-2. In FIG. 8, "NT" stands for not treated with the SAC and "+SAC" stands for treated with SAC, where the units of the y-axis are pictograms per milliliter. Thus, FIG. 8 evidences the ability to perfuse the lymphatic tissue within the chamber (e.g., chamber 114 and/or chamber 126) with an antigen (SAC) and obtain a biological response (e.g., production of cytokine IL-2) that mimics the response in vivo.

In addition, the OOC can be directly analyzed (e.g., through microscopy) in addition to the effluent from the first and second fluid paths can be analyzed. For example, clonal proliferation of T and B lymphocytes can be visualized by microscopy and quantified by flow cytometry and polymerase chain reaction (PCR) for overrepresented T lymphocyte receptor and B lymphocyte receptor sequences.

Although the above discussion has focused on the human lymphoid tissue-on-chip in isolation, the human lymphoid tissue-on-chip can be microfluidically connected to other microfluidic devices for investigating the interaction of the human lymph node with other organs and tissue of the human body. For example, the human lymphoid tissue-on-chip can be connected to a lung-on-chip or a liver-on-chip, where the lung and/or liver-on-chip includes metastases to model the impact on T lymphocyte polarization, lymphocyte clustering, and responses to activation in a tumor draining lymph node. The human lymph-node-on-chip can be linked fluidically via its blood or lymphatic channels (e.g., first, second, or more fluid paths) to other organ-on-chips to explore more complex organ-organ physiological or pathophysiological coupling in studies on, for example, cancer metastasis, infection propagation, and body-wide immune responses or auto-immune responses. Thus, the human lymphoid tissue-on-chip provides the opportunity to test the efficacy of therapeutic antibodies, such as anti-PD1, in alleviating tumor-induced immunosuppression in the draining lymph node.

The human lymph node-on-a-chip also can be applied to the study of vaccinology, immunology, and cancer immunotherapy. Thus, specific topics that can be investigated using the concepts of the present disclosure include, for example, the trafficking of HIV into the human lymph node, the metastases of cancer into the human lymph node, and the screening of vaccine candidates for infectious diseases.

The human lymph-node-on-chip also can be used to develop therapeutics, such as high affinity antibodies and to identify the sequences of these antibodies. The human lymph-node-on-chip also can be used to develop drug delivery systems that specifically target lymph nodes, for example, using directed evolution strategies (e.g., phage display peptide or antibody selection systems).

The human lymphoid tissue-on-chip also can be applied to understand the following exemplary issues: (1) the study of trafficking of viruses (e.g., HIV) or other pathogens to the lymph node; (2) the identification of the best vaccine candidates for infectious diseases; (3) patient stratification for anti-cancer immunotherapy; (4) personalization of anti-cancer immunotherapy; (5) identification of immunotherapy toxicity; (6) establishment and treatment of lymph node metastases; (7) identifying new treatments for lymphomas; (8) identifying design parameters for building other immune organs-on-chip, such as Peyer's patch; and (9) identifying design parameters for implantable lymph nodes, to name just a few examples. Further, the human lymphoid tissue-on-chip enables in vitro trials of the staggering number of combinatorial immunotherapies being considered for cancer treatment and identification of the best combinations for clinical trial.

The human lymphoid tissue-on-chip enables the study of patient-specific lymph node biology before and after therapy without invasive procedures. The human lymphoid tissue-on-chip also enables the assessment of the cytokine release by tissue resident lymphocytes, the study of chimeric antigen receptor (CAR) T-cell therapy trafficking and expansion, the establishment, expansion and impact of lymph node metastases in real time with allowing visualization of key events by live microscopy.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A microfluidic device comprising:
   a body comprising a first microchannel, a first chamber and a second chamber, the first microchannel having an inlet and an outlet to an exterior of the body, the first chamber being in fluidic communication with the first microchannel and comprising a first matrix comprising B lymphocytes, and the second chamber comprising a second matrix comprising T lymphocytes.

2. The microfluidic device of claim 1, wherein the first matrix is an extracellular matrix.

3. The microfluidic device of claim 2, wherein the extracellular matrix comprises a hydrogel.

4. The microfluidic device of claim 1, further comprising a membrane separating the first microchannel from the first chamber, wherein the membrane permits fluid and solids to pass between the first microchannel and the first chamber.

5. The microfluidic device of claim 1, wherein the body further comprises a second microchannel, wherein the second chamber is between the first chamber and the second microchannel.

6. A method, comprising
   a) providing a microfluidic device comprising a body comprising a first microchannel, a first chamber and a second chamber, the first microchannel having an inlet and an outlet to an exterior of the body, the first chamber being in fluidic communication with the first microchannel;
   b) providing a first matrix comprising T lymphocytes in said first chamber, and
   c) providing a second matrix comprising B lymphocytes in said second chamber.

7. The method of claim 6, wherein the first matrix is an extracellular matrix.

8. The method of claim 7, wherein the extracellular matrix comprises a hydrogel.

9. The method of claim 6, further comprising a membrane separating the first microchannel from the first chamber, wherein the membrane permits fluid and solids to pass between the first microchannel and the first chamber.

10. The method of claim 6, wherein the body further comprises a second microchannel, wherein the second chamber is between the first chamber and the second microchannel.

* * * * *